(12) United States Patent
Staton et al.

(10) Patent No.: US 6,518,556 B2
(45) Date of Patent: Feb. 11, 2003

(54) LARGE DYNAMIC RANGE LIGHT DETECTION

(75) Inventors: Kenneth L. Staton, San Carolos, CA (US); Andreas N. Dorsel, Menlo Park, CA (US); Arthur Schleifer, Portola Valley, CA (US)

(73) Assignee: Agilent Technologies Inc., Palo Alto, CA (US)

( * ) Notice: Subject to any disclaimer, the term of this patent is extended or adjusted under 35 U.S.C. 154(b) by 0 days.

(21) Appl. No.: 10/068,419

(22) Filed: Feb. 4, 2002

(65) Prior Publication Data

US 2002/0070330 A1 Jun. 13, 2002

Related U.S. Application Data

(62) Division of application No. 09/313,102, filed on May 17, 1999, now Pat. No. 6,355,921.

(51) Int. Cl.$^7$ ............................................. H01J 40/14
(52) U.S. Cl. ............................... 250/207; 250/214 VT
(58) Field of Search ............................ 250/207, 214 R, 250/214 VT; 327/514; 313/105 CM

(56) References Cited

U.S. PATENT DOCUMENTS

| | | | |
|---|---|---|---|
| 3,571,493 A | * 3/1971 | Baker et al. | 353/85 |
| 3,843,257 A | * 10/1974 | Wooten | 356/316 |
| 3,941,478 A | * 3/1976 | Dougherty et al. | 356/30 |
| 4,590,368 A | 5/1986 | Govaert | 250/207 |
| 4,857,722 A | 8/1989 | Kumazawa et al. | 250/207 |
| 5,257,202 A | 10/1993 | Feddersen et al. | 364/498 |
| 5,260,029 A | 11/1993 | Hosoi et al. | 422/82.08 |
| 5,264,693 A | 11/1993 | Shimabukuro et al. | 250/207 |
| 5,475,227 A | 12/1995 | LaRue | 250/207 |
| 5,493,111 A | 2/1996 | Wheeler et al. | 250/207 |
| 5,504,337 A | 4/1996 | Lakowicz et al. | 250/461.2 |
| 5,528,046 A | 6/1996 | Ishikawa | 250/461.2 |
| 5,582,705 A | 12/1996 | Yeung et al. | 204/603 |
| 5,631,734 A | 5/1997 | Stern et al. | 356/317 |

FOREIGN PATENT DOCUMENTS

| | | | |
|---|---|---|---|
| DE | 3915692 | 11/1990 | G01N/21/64 |
| DE | 19618601 | 11/1997 | G01J/1/44 |
| SU | 1350508 | 7/1986 | |
| WO | WO88/01751 | 10/1988 | |

OTHER PUBLICATIONS

Examiner Gareth Lewis, British Patent Office, Search Report under Section 17 Dated Sep. 5, 2000, British application No. GB0011109.6, 1 page.

* cited by examiner

Primary Examiner—Stephone B. Allen

(57) ABSTRACT

System for large dynamic range light detection. In one aspect, the system includes a hybrid counting/integrating system for processing a signal from a photomultiplier tube. In another aspect, large dynamic range is achieved in a cascaded detector system utilizing at least one asymmetric beam splitter for delivering a larger fraction of incident light to one photomultiplier tube and for delivering a smaller fraction of the incident light to another photomultiplier tube.

6 Claims, 2 Drawing Sheets

LARGE DYNAMIC RANGE LIGHT DETECTION

This is a divisional of application Ser. No. 09/313,102 filed on May 17, 1999 now U.S. Pat. No. 6,355,921.

BACKGROUND OF THE INVENTION

This invention relates to large dynamic range light detection and more particularly to a system for use in fluorescence readers to accommodate large dynamic ranges while maintaining optimal signal-to-noise performance.

Fluorescence readers are often used for re-sequencing or gene expression studies. In these systems, light such as that from a laser is directed onto a target which may include molecules capable of fluorescing. The emitted fluorescent light is then detected and analyzed. Detection is often accomplished using a photomultiplier tube in which incident light falls upon a photocathode thereby liberating primary electrons via the photoelectric effect. These primary electrons encounter structures known as dynodes to release secondary electrons. The electrons migrate to an anode and produce a current pulse. The dynamic range of the photomultiplier tube (PMT) is the ratio of the strongest expected signal to the weakest expected signal. At the low end of the signal range it is advantageous to count photons while at the high end such counting may no longer be possible due to pulse overlap and for other reasons.

A brute-force approach to the large dynamic range problem is to increase measurement (averaging) time to extend the detection range toward lower signal levels. While other solutions are available (compare, for example, a quantum photometer in "The Art of Electronics" by Horowitz and Hill, P. 998, ISBN 0-521-37095-7, Second Edition 1989), they do not permit the fast (pixel times on the order of microseconds) simultaneous measurement of current and fast photon counting. The present invention will increase dynamic range without increasing measurement or averaging time.

SUMMARY OFT THE INVENTION

In one aspect, the system according to the invention for large dynamic range light detection includes a photomultiplier tube for receiving incident light photons and for generating an output electrical signal in response to the incident light, A discriminator/counter responds to the output signal from the photomultiplier tube to count photons for output signals below a first selected level. A charge integrator responds to the output signal from the photomultiplier tube to integrate the output signal for output signals above a second selected level. Control circuitry is provided responsive to the discriminator/counter and to the charge integrator so that dynamic range is increased. In one embodiment, control circuitry is provided to record outputs from the discriminator/counter and from the charge integrator. In another embodiment, the control circuitry selects an output either from the discriminator/counter or from the charge integrator or a linear combination of the two based on strength of the output signal and stores the selected output. The control circuitry may be a digital signal processor.

In another aspect, the system of the invention for increasing dynamic range includes a photomultiplier tube for receiving incident light photons and generating output electrical signal in response to the incident light. An analog-to-digital converter responds to the output signal to generate a digital signal, and a digital signal processor operates on the digital signal. The digital signal processor is programmed to analyze the signal to determine whether the signal is within a photon counting range or within an integrating range. The digital signal processor is further programmed to mimic photon counting when the signal is in the photon counting range or to integrate the signal when the signal is in the integrating range and to generate an output. A photomultiplier tube preamplifier circuit may be provided to broaden pulses from the photomultiplier tube to cover several sampling intervals.

In yet another aspect, the system according to the invention for large dynamic range light detection includes at least one asymmetric beam splitter for receiving incident light and to direct a larger fraction of the incident light to one photomultiplier tube and to direct a smaller fraction of the incident light to at least one other photomultiplier tube. In a preferred embodiment, the photomultiplier tube receiving the larger fraction of incident light is operated in a photon counting mode and the photomultiplier tube receiving the smaller fraction of the incident light is operated in an integrating mode. A suitable larger fraction is 90% of the incident light and a suitable smaller fraction is 10% of the incident light. A suitable beam splitter is uncoated glass. A digital signal processor may be provided for operating on the signals from the photomultiplier tubes. It is also preferred that a fast modulator be provided to attenuate the incident light based on an actual signal thus resulting in dynamic compression.

The different aspects of the present invention extend signal dynamic range to allow photon counting at the low end of the dynamic range and extend the range up to a maximum light load that the light detector can accommodate. The systems of the invention allow covering dynamic ranges that are limited by the photon counting detection limit at the lower end and by the destruction threshold of the PMT at the high end. The present invention makes it possible to achieve dynamic ranges of $10^4$ and more.

DESCRIPTION OF THE PREFERRED EMBODIMENT

Figure 1:
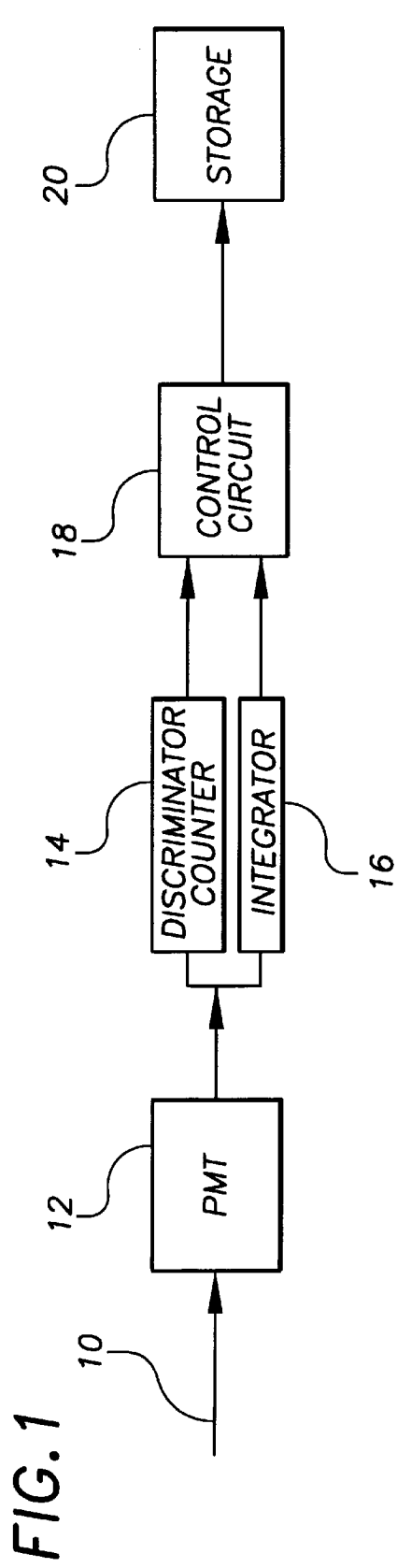
FIG. 1 is a block diagram illustrating one embodiment of the invention.

With reference first to FIG. 1, a hybrid approach to increasing dynamic range will be described. Incident light illustrated by an arrow 10 such as light from fluorescing molecules is detected by a photomultiplier tube (PMT)12. An output of the PMT 12 forms an input both to a discriminator/counter 14 and a charge integrator 16. The discriminator/counter 14 covers a range of low signals and eliminates most of the excess noise of the PMT 12. In a preferred embodiment, the output current of the PMT 12 is first converted into a voltage using an electrometer which may be considered part of the PMT 12 block in FIG. 1. The integrator 16 covers stronger signal ranges where excess noise is no longer a problem, up to the PMT's saturation/destruction limit. For a typical system, the low and high signal regimes will overlap by a factor of two or more and thus can be gauged to give a continuous transition from counting to integration. The outputs of the discriminator/ counter 14 and integrator 16 are read out and reset by a control circuit 18. The control circuit 18 either records both results in storage 20 or chooses one of them based on signal strength and stores only that one in the storage 20. The control circuit 18 may be a digital signal processor (DSP).

Figure 2:
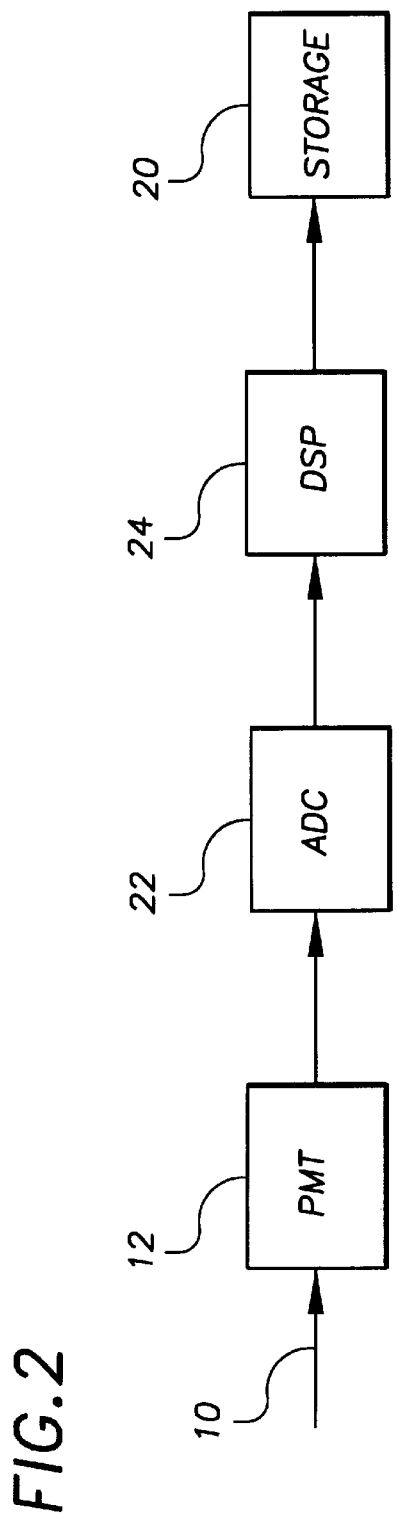
FIG. 2 is a block diagram illustrating an embodiment of the invention utilizing a digital signal processor.

FIG. 2 is an embodiment of the invention utilizing fast digital signal processors which can perform both the counting and integrating functions. In this embodiment, the output from the PMT 12 is digitized in an analog-to-digital converter 22 and is processed by a digital signal processor 24. The fast DSP 24 analyzes the output of the analog to digital converter 22 in a manner such that not a single photon event is missed if possible. This functionality can be achieved by having a PMT preamplifier circuit (not shown) that broadens the PMT pulses just enough to cover a few sampling intervals while not yet reducing pulse height excessively. The DSP 24 analyzes the signal (e.g., by looking at its integrated value first) to find out whether it is in the counting range or the integrating range and then either applies an algorithm that mimics photon counting (i.e., a pulse height discrimination and counting) or integrates the signal if not previously performed. In a crossover region between the high and low signal regimes either a transition point or a gradual transition using the two signals is possible. The DSP 24 can also compensate non-linearities of the signal-versus-light level response. This approach, too, gets rid of the PMT excess noise at the low end of the signal range.

Figure 3:
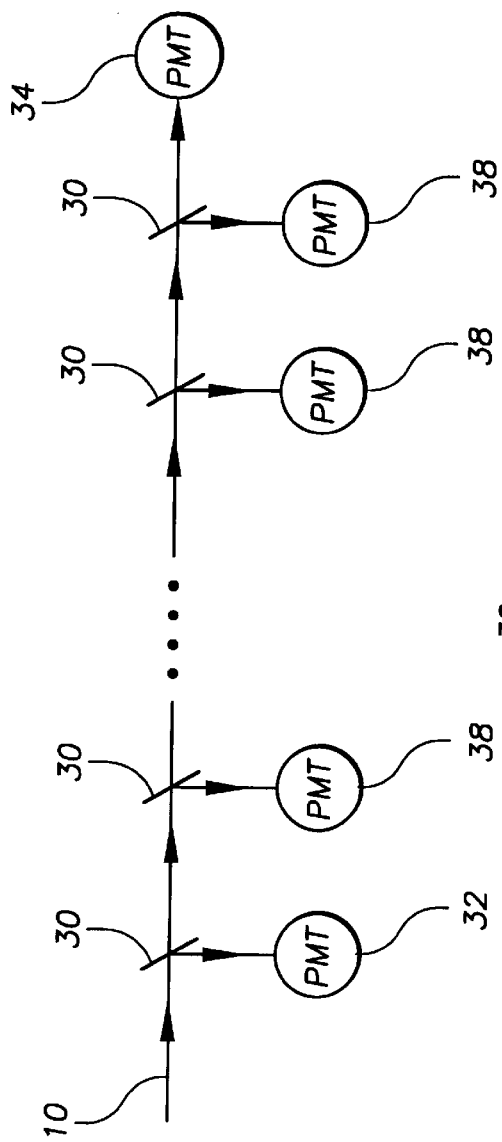
FIG. 3 is a schematic diagram illustrating yet another aspect of the present invention.

A second cascaded approach to increasing dynamic range is shown in FIG. 3. Incident light 10 encounters an asymmetric beam splitter 30 which directs most (e.g. 90%) of the incident light to a photomultiplier tube 32 (PMT). The remaining light (e.g. 10%) passes through the beamsplitter and may be directed to a last PMT 34 or be split up further by additional beamsplitters that direct the larger fraction of the light passed on by the previous beam splitter to intermediate PMTs 38. The PMT 32 which receives the largest fraction of the signal is preferably run in photon counting mode while the PMTs 34 and 38 are operated in charge integration mode. As in the embodiment of FIGS. 1 and 2, additional circuitry (e.g. a DSP) can be provided in the embodiment of FIG. 3 to choose the appropriate combination of output signals to be either combined into one output signal or to be recorded/stored in parallel.

The asymmetric beam splitters 30 would in this case normally have to be coated plates. Also, their reflectivities may be different from one another for some designs. The angle of incidence shown serves for illustration purposes only. In the case shown, typical transmissions might be 10% and typical reflectivities might be 90%. If each of the PMTs has a dynamic range of $10^3$, then the total dynamic range would be $10^4$ for two PMTs and even more for additional PMTs.

Figure 4:
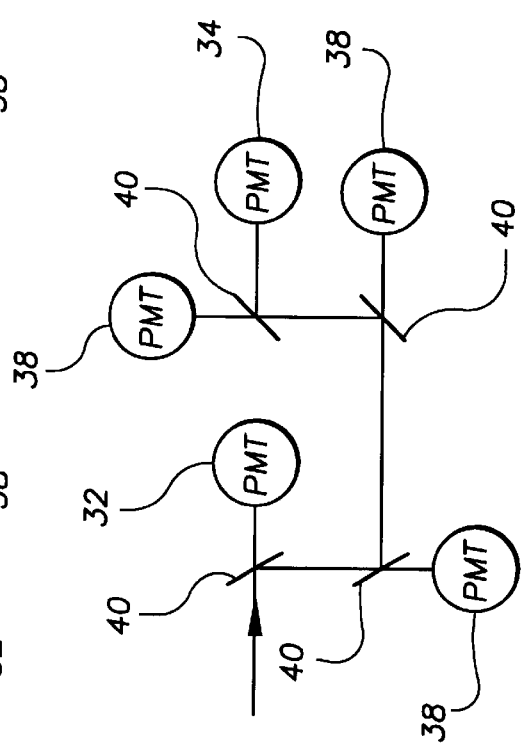
FIG. 4 is a schematic diagram illustrating an embodiment of the invention using uncoated beam splitters.

Another embodiment is shown in FIG. 4. In this arrangement, the beam splitters 40 can be uncoated substrates which are less expensive than coated substrates. The uncoated substrate will reflect about 10% and transmit about 90% of the incident light. Again, the PMT 32 gets the strongest signal and the PMT 34 gets the weakest signal with the PMTs 38 getting increasingly weaker signals as one moves from the PMT 32 to the PMT 34.

The designs illustrated in FIGS. 3 and 4 may be limited by the damage threshold of the PMT 32 which sees the larger share of the signal. There are several ways to deal with the potential damage problem. First of all, one could modulate the illumination power by modulating the source of light directly or using an external modulator (e.g. for diode laser or LED source). Alternatively, the emitted fluorescent light can be modulated to reduce the amount of light going to PMT 32 while leaving the full signal on the PMT 34. This approach would protect both the cathode and dynodes of the PMT 32. Alternatively, the PMT bias voltage can be modulated for one or more electrodes, which will protect dynodes but not the photocathode.

Both the hybrid counting/integrating system and the cascaded detector system described above extend signal dynamic range by allowing photon counting at the low end of the dynamic range and extended up to the maximum light load the detector can handle. Both approaches allow covering dynamic ranges that are limited by the photon counting detection limit at the lower end and by the destruction threshold of the PMT at the high end. Dynamic ranges well in excess of $10^4$ and more are achievable with the designs of this invention.

It is intended that all modifications and variations of the above-described invention be included within the scope of the appended claims.

What is claimed is:

1. System for large dynamic range light detection comprising:
    at least one asymmetric beam splitter for receiving incident light and to direct a larger fraction of the incident light to one photomultiplier tube and to direct a smaller fraction of the incident light to at least one other photomultiplier tube,
    wherein the photomultiplier tube receiving the larger fraction of incident light is operated in a photon counting mode and wherein the photomultiplier tube receiving the smaller fraction of the incident light is operated in an integrating mode.

2. The system of claim 1 wherein the larger fraction is approximately 90% and the smaller fraction is approximately 10%.

3. The system of claim 1 wherein the beam splitter is uncoated glass.

4. The system of claim 1 further including a digital signal processor to choose an appropriate combination of output signals to be combined either into one output signal or to be recorded/stored in parallel.

5. The system of claim 1 further including a fast modulator to attenuate light incident on a target sample.

6. The system of claim 1 further including a fast modulator to attenuate incident light on at least one of the photomultipliers.

* * * * *